(12) United States Patent
Park et al.

(10) Patent No.: US 8,394,775 B2
(45) Date of Patent: Mar. 12, 2013

(54) COSMETIC COMPOSITION CONTAINING HYDROLYSATES OF ICARIIN

(75) Inventors: Jun Seong Park, Gyeonggi-do (KR); Ho Sik Rho, Gyeonggi-do (KR); Duck Hee Kim, Seoul (KR); Ih Seop Chang, Gyeonggi-do (KR)

(73) Assignee: Amorepacific Corporation, Seoul (KR)

( * ) Notice: Subject to any disclaimer, the term of this patent is extended or adjusted under 35 U.S.C. 154(b) by 821 days.

(21) Appl. No.: 12/095,654

(22) PCT Filed: Oct. 30, 2006

(86) PCT No.: PCT/KR2006/004448
§ 371 (c)(1), (2), (4) Date: Aug. 11, 2008

(87) PCT Pub. No.: WO2007/064085
PCT Pub. Date: Jun. 7, 2007

(65) Prior Publication Data
US 2009/0170787 A1    Jul. 2, 2009

(30) Foreign Application Priority Data
Nov. 30, 2005    (KR) .................. 10-2005-0115649

(51) Int. Cl.
*A61K 8/60* (2006.01)
*A61Q 19/08* (2006.01)
(52) U.S. Cl. ............................................. 514/27; 514/8
(58) Field of Classification Search ............ 514/27; 536/8
See application file for complete search history.

(56) References Cited

U.S. PATENT DOCUMENTS

| 6,399,579 B1 * | 6/2002 | Lenoble et al. | 514/25 |
| 6,476,203 B1 | 11/2002 | Zhao | |
| 7,314,634 B2 * | 1/2008 | Hernandez et al. | 424/401 |
| 2002/0119107 A1 * | 8/2002 | Varani et al. | 424/59 |

FOREIGN PATENT DOCUMENTS

| JP | 11-158078 | 6/1999 |
| KR | 10-1994-0001005 | 2/1994 |
| KR | 1994-0001005 | 2/1994 |
| WO | 99/47137 | 9/1999 |

OTHER PUBLICATIONS

Xiao et al, Phytochemistry, 1996, 4392), 527-530.*
Liu et al J. Pharm. Pharmacol. Dec. 2004, 56, 1557-62.*
Brennan et al Photochemistry and Photobiology, 2003, 78(1), 43-48.*
Korean Intellectual Property Office, Notice of Preliminary Rejection and English translation in Korean application Serial No. 10-2005-0115649 mailed Apr. 2, 2007.
International Search Report for International Application No. PCT/KR2006/004448, mailed Jan. 30, 2007.
Li et al, Status & Prospect of Research on Medicinal Plants of *Epimedium* L., Chinese Traditional and Herbal Drugs, vol. 32, p. 289-295, Feb. 28, 2005.
Third Notification of Office Action w/English translation in CN Application No. 2006800447555 issued Apr. 20, 2011.
"Status and Prospect of Research on Medicinal Plants of *Epimedium* L", Li, Zuo-zhou, et al, Chinese Traditional and Herbal Drugs, vol. 32, pp. 289-295 (Feb. 28, 2005).
Park et al, "Statistically Designed Enzymatic Hydrolysis for Optimized Production of Icariside II as a Novel Melanogenesis Inhibitor", J. Microbiol. Biotechnol. (2008), 18(1), 110-117.

* cited by examiner

*Primary Examiner* — Shaojia Anna Jiang
*Assistant Examiner* — Ganapathy Krishnan
(74) *Attorney, Agent, or Firm* — Nixon & Vanderhye P.C.

(57) ABSTRACT

The present invention relates to a cosmetic composition containing hydrolysates of icariin, and more particularly, a cosmetic composition containing hydrolysates of icariin including icaritin, icariside I and icariside II. The hydrolysates of icariin is prepared by a method comprising the steps of: (a) obtaining an extract from a plant containing icariin using water or an organic solvent; and (b) hydrolyzing the plant extract with an acid, a base, an enzyme or a microorganism producing the enzyme. The cosmetic composition according to the present invention is employed for anti-oxidant, anti-aging, whitening or anti-wrinkling effects.

2 Claims, No Drawings

COSMETIC COMPOSITION CONTAINING HYDROLYSATES OF ICARIIN

This application is the U.S. national phase of International Application No. PCT/KR2006/004448, filed 30 Oct. 2006, which designated the U.S. and claims priority to KR 10-2005-0115649, filed 30 Nov. 2005, the entire contents of each of which are hereby incorporated by reference.

TECHNICAL FIELD

The present invention relates to a cosmetic composition containing hydrolysates of icariin, and more particularly, a cosmetic composition containing hydrolysates of icariin, including icaritin, icariside I and icariside II, in which the hydrolysates of icariin is prepared by a method comprising the steps of: (a) obtaining an extract from a plant containing icariin using water or an organic solvent; and (b) hydrolyzing the plant extract with an acid, a base, an enzyme or a microorganism producing the enzyme.

BACKGROUND ART

Plants of the *Epimedium* genus belonging to the Berberidaceae family are classified into three species of *E. brevicornum*, *E. sagittatum* and *E. koreanum*, as described in Chinese pharmacopoeia. It has been reported that the plants of the *Epimedium* genus comprise main components of flavonoid, alkaloid and lignan. Particularly, the herb medicine prepared by drying the whole plant except for the root of *Epimedium koreanum* Nakai is called Epimeii Herb and has been used for treatment of total paralysis and amnesia, and an aphrodisiac and analeptic agent.

It is known that oxygen free radical generated by various physical, chemical and environmental factors such as enzyme system and reductive metabolism in the body, chemicals, pollutants and photochemical reaction induces various diseases including cell aging or cancers by non-selective, irreversible destruction against lipid, cell constituting materials such as protein, sugar and DNA. Also, the oxygen free radical is a cause of many diseases since various peroxides in the body including lipid peroxides generated by peroxidization of lipid by the oxygen free radical bring about oxidative destruction of cells, leading various functional disorders.

Therefore, anti-oxidants such as free radical scavengers capable of removing free radical or substances inhibiting formation of peroxides such free radical are expected to be inhibitants or therapeutic agents against aging and various diseases caused by these peroxides.

For development of natural anti-oxidants, many materials derived from natural sources were studied. However, most of the materials derived from natural sources were used in a simple extract form and substances, to which the effect of the extract was attributed, were not clearly shown. The materials have been used in the cosmetic composition by experience and information by word of mouth.

Meanwhile, the skin aging is largely classified according to its cause. One is natural aging (Intrinsic aging), in which the structure and physiological functions of the skin are continuously degraded as one becomes older. The other one, that is extrinsic aging is caused by external stress accumulated such as solar rays. Particularly, ultraviolet rays (UV) among the sun beams are the main cause of aging. When the skin is exposed to UV rays for a long period of time, the stratum corneum is thickened and collagen and elastin are denatured, whereby the skin loses its elasticity. These collagen and elastin are controlled by many factors. By the expression of matrix metallo protease such as collagenase and elastase, the synthesized collagen and elastin are decomposed and consequently, the collagen level in the skin is reduced.

In order to inhibit decrease of collagen and elastin which are causes of reduction of elasticity, many substances have been developed and used. Among them, retinoids such as retinol and retinoic acid show improvement of elasticity (Dermatology therapy, 1998, 16, 357 to 364) and a protein fraction obtained from Leguminosae seeds showed increase in elasticity (U.S. Pat. No. 5,322,839).

However, these retinoids have defects that they may cause irritation when they are applied on the skin even in a small amount. They are mainly materials derived from natural materials and thus, it is not clarified that which components of the extract show the effect. Accordingly, it is difficult to maintain and control the activity of the extract.

Meanwhile, many factors participate in determination of the skin color of human bodies. Particularly, activity of melanocyte, where melanin pigment is formed, distribution of blood vessels, skin thickness and presence of a pigment such as carotenoid and bilirubin in the outside or inside of the body are important.

The most important factor among them is melanin, a black pigment, produced by action of various enzymes such as tyrosinase in melanocyte of the human body. The formation of this melanin pigment is affected by genetic factors, physiological factors associated with hormone secretion and stress and environmental factors such as irradiation of UV rays.

The melanin pigment generated in melanin cells of the human skin is a high-molecular weight phenolic compound having a composite structure of a black pigment and a protein and intercepts UV rays from the sun to protect skin organisms under the dermis while protecting proteins and genes in the skin by capturing free radicals produced in the skin.

As described above, melanin generated by the external stress stimulation is a stable substance which does not disappear, even when the stress is released, until it is discharged through keratinization of the skin. However, when melanin is generated excessively over the needed amount, hyper-pigmentation, cosmetically undesirable conditions, such as discoloration, freckles or speckles may be induced.

Also, as the number of people who enjoy the outer activities is increased due to the increase of leisure population, there is a need to prevent pigmentation of melanin by UV rays.

In order to satisfy the above-described need, ascorbic acid, kojic acid, arbutin, hydroquinone, glutathion or derivatives thereof, or substances having inhibition activity on tyrosinase have been used in cosmetic compositions of pharmaceutical products. However, the use of these substances is limited because of insufficient whitening effect, safety upon use on the skin, formulation and safety problems occurring when added to cosmetic compositions.

DISCLOSURE

Technical Problem

Accordingly, in order to solve the above-mentioned problems and to obtain materials excellent in anti-oxidant, anti-aging and whitening effects, the present inventors have searched many natural substances and found that icariin, which is a flavonoidic component in the extract of plants belonging to the *Epimedium* genus, has those effects and hydrolysates of icariin prepared by hydrolyzing icariin using an acid, a base, an enzyme or a microorganism producing the enzyme are more excellent in anti-oxidant, anti-aging and whitening effects.

Therefore, it is an object of the present invention to provide a cosmetic composition containing hydrolysates of icariin as an effective ingredient.

It is another object of the present invention to provide a method for preparing hydrolysates of icariin by hydrolyzing the icariin derived from plants of the *Epimedium* genus with an acid, a base, an enzyme or a microorganism producing the enzyme for use in a cosmetic composition as an effective ingredient.

Technical Solution

In order to accomplish the above objects, according to the features of the present invention, there is provided a cosmetic composition containing hydrolysates of icariin expressed by the following formula 1:

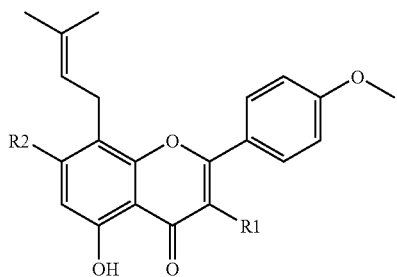

[Formula 1]

in which R1 is OH or rhamnopyranose, R2 is OH or glucopyranose, provided that both R1 and R2 are not rhamnopyranose or glucopyranose at the same time.

According to the present invention, the composition is a cosmetic composition for anti-oxidant, anti-aging, whitening or anti-wrinkle effects.

The hydrolysates of icariin contained in the cosmetic composition according to the present invention is prepared by a method comprising the steps of: (a) obtaining an extract from a plant containing icariin using water or an organic solvent; and (b) hydrolyzing the plant extract with an acid, a base, an enzyme or a microorganism producing the enzyme.

The extract in the step (a) is extracted from a plant belonging to the *Epimedium* genus and the organic solvent may be at least one selected from the group consisting of ethanol, methanol, butanol, ether, ethylacetate and chloroform, or a mixture thereof with water, with preference being 80% ethanol.

Also, the acid used in the step (b) may be at least one selected from the group consisting of hydrochloric acid, sulphuric acid, and nitric acid, or a mixture thereof with at least one selected from the group consisting of ethanol, methanol and butanol. Here, the concentration of the acid is 0.1 to 2N and the content of the alcohol in the alcoholic solvent mixture is 10 to 50%. The reaction temperature is 50 to 100° C. and the reaction time is 0.5 to 8 hours.

The base used in the step (b) may be at least one selected from the group consisting of sodium hydroxide and potassium hydroxide, or a mixture thereof with at least one selected from the group consisting of ethanol, methanol and butanol. Here, the concentration of the base is 0.1 to 2N and the content of the alcohol in the alcoholic solvent mixture is 10 to 50%. The reaction temperature is 50 to 100° C. and the reaction time is 0.5 to 24 hours.

The enzyme or the microorganism producing the enzyme used in the step (b) may be an enzyme decomposing a sugar linkage or a microorganism producing the enzyme decomposing a sugar linkage. The enzyme removes the sugar part in icariin to produce hydrolysates of icariin.

The enzyme may be at least one selected from the group consisting of glucosidase, arabinosidase, rhamnosidase, xylosidase, cellulase, hesperidinase, naringinase, glucuronidase, pectinase, galactosidase and amyloglucosidase.

Also, the microorganism producing the enzyme may be at least one selected from the group consisting of *Aspergillus* genus, *Bacillus* genus, *Penicillium* genus, *Rhizopus* genus, *Rhizomucor* genus, *Talaromyces* genus, *Bifidobacterium* genus, *Mortierella* genus, *Cryptococcus* genus and *Microbacterium* genus.

BEST MODE

The icariin and hydrolysates of icariin, that is, icaritin, icarisides I and II have the following formula:

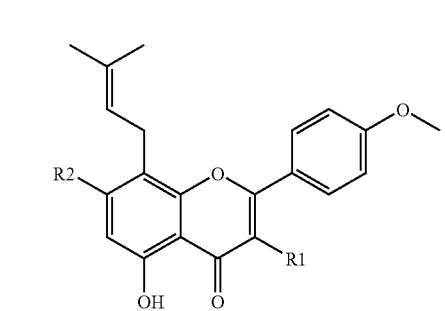

[Formula 1]

| compound | R1 | R2 |
| --- | --- | --- |
| Icariin | rhamnopyranose | Glucopyranose |
| Icariside I | OH | Glucopyranose |
| Icariside II | rhamnopyranose | OH |
| Icaritin | OH | OH |

Now, the process for preparing hydrolysates of icariin is described in detail.

In the step (a), the following method for obtaining a plant extract containing icariin with water or an organic solvent from the plant is performed. Firstly, the plant is put into about 1 to 6 folds, preferably about 3 folds of water, or at least one organic solvent selected from the group consisting of ethanol, methanol, butanol, ether, ethylacetate and chloroform or a mixture thereof with water, stirred 1 to 5 times at room temperature and defatted. The defatted plant is then put into about to 8 folds, preferably about 4 folds water or an organic solvent, extracted 1 to 5 times under reflux and settled for 1 to 3 days at 10 to 20° C.

The settled is separated into residue and filtrate through filtration and centrifugation. The filtrate is concentrated under pressure to obtain the extract. The extract is suspended in water and decolorized with ether. The water layer is extracted off 1 to 5 times with butanol and the resulting organic solvent layer is concentrated under pressure to obtain the butanol extract. The butanol extract is taken into a small mount of methanol and mixed with a large amount of ethylacetate. The resulting precipitation is dried to give icariin.

In the step (b), icariin obtained from the step (a) is hydrolyzed with an acid, a base, an enzyme or a microorganism producing the enzyme to produce hydrolysates of icariin.

Here, in the case of hydrolysis with an acid, the plant extract is mixed with an acid or a mixture of an acid and an alcohol, preferably 50% ethanol mixture, at a concentration of 0.1 to 2N, preferably 1N, and heated to reflux in a water bath at 50 to 100° C., preferably 80° C., for 1 to 48 hours, preferably 8 hours, to obtain the reactant.

In the case of hydrolysis with a base, the plant extract is mixed with a base or a mixture of a base and an alcohol, preferably 50% butanol mixture, at a concentration of 0.1 to 2N, preferably 1N, and heated to reflux in a water bath at 50 to 100° C., preferably 100° C., for 1 to 48 hours, preferably 8 hours, to obtain the reactant.

In the case of hydrolysis with an enzyme, the plant extract is dissolved in 5 to 20 folds, preferably about 10 folds of an acid buffer solution. The enzyme is added to the solution and stirred in a water bath at about 37° C. for about 40 to 55 hours, preferably about 48 hours. When the substrate completely disappears by confirming the elimination rate of the substrate by thin layer chromatography, the hydrolysis reaction is finished by heating in hot water (80 to 100° C.) for 5 to 15 minutes to obtain the reactant.

In the case of hydrolysis with a microorganism producing the enzyme, the plant extract is dissolved in 5 to 10 folds, preferably about 10 folds of ionized water, sterilized at about 121° C. for 30 minutes, cooled to about 30° C., inoculated with a microorganism, which has been cultured, in an amount of 5 to 10% based of the total amount of the solution and cultivated at 30° C. for 2 to 5 days, preferably 5 days. When the substrate completely disappears by confirming the elimination rate of the substrate by thin layer chromatography, the hydrolysis reaction is finished by heating in hot water (80 to 100° C.) for 5 to 15 minutes. The resulting culture fluid is centrifuged at 5,000 to 10,000 rpm. The precipitation is washed 3 times with distilled water and centrifuged to obtain precipitation as the reactant.

The reactant obtained by hydrolysis with an acid, a base, an enzyme or a microorganism producing the enzyme as described above is concentrated under pressure to remove the solvent. The residue is added to an alcohol, stirred 1 to 5 times. The precipitated salts are removed by filtration and the filtrate is concentrated under pressure to obtain a crude product, which is separated by silica gel column chromatography (chloroform:methanol=8:1 to 4:1) to obtain hydrolysates of icariin.

The hydrolysates of icariin prepared according to the present invention has excellent anti-oxidant effect by inhibition of DPPH and ROS formation, anti-aging effect by promotion of collagen biosynthesis and inhibition of collagenase expression and whitening effect by inhibition of melanin production and improvement of pigmentation caused by UV rays.

Therefore, according to the present invention, there is provided a cosmetic composition for anti-oxidant effect comprising the hydrolysates of icariin as an effective ingredient.

Also, according to the present invention, there is provided a cosmetic composition for anti-aging effect comprising the hydrolysates of icariin as an effective ingredient.

Also, according to the present invention, there is provided a cosmetic composition for whitening effect comprising the hydrolysates of icariin as an effective ingredient.

Also, according to the present invention, there is provided a cosmetic composition for wrinkle improving effect comprising the hydrolysates of icariin as an effective ingredient.

The cosmetic composition may be formulated into a cosmetic composition or a pharmaceutical composition and the content of the hydrolysates of icariin in the composition is in the range of 0.0001 to 10 wt % based on the total weight of the composition. The composition may comprise one or more of the hydrolysates of icariin.

MODE FOR INVENTION

Now, the present invention is described in detail by the following examples. However, it should be understood that the examples are only for explanation of the present invention and the present invention is not limited thereto.

Example 1

Preparation and Identification of Icariin

<Preparation of Icariin>

2 kg of Dried leaves of *Epimedium koreanum* Nakai was put into 6 l of hexane, extracted 3 times at room temperature, while stirring, to remove fat. 1 kg of the defatted leaves was put into 4 l of 80% methanol, extracted under reflux 3 times and settled at 15° C. for 1 day. Then, the residue and the filtrate were separated by filtration with filter cloth and centrifugation. The filtrate was concentrated under pressure to obtain an extract. The extract was suspended in water, extracted 5 times with 1 l of ether to remove pigments. The water layer was extracted 3 times with 500 ml of 1-butanol. The combined 1-butanol layers were concentrated under pressure to obtain 1-butanol extract. The 1-butanol extract was dissolved in a small amount of methanol and a large amount of ethylacetate was added thereto to form precipitation. The precipitation was dried to give 80 g of *Epimedium koreanum* Nakai containing icariin.

<Identification of Icariin>

20 g of the extraction prepared in Example 1 was purified by silica gel column chromatography, charged with silica gel 100 g. Here, chloroform and methanol were used as the eluting solvents. Fractions were obtained by increasing the ratio of chloroform and methanol from 10:1 to 2:1 and 2.3 g of icariin was produced therefrom. The resulting product was identified (Varian Gemini 2000 300 MHz, Varian) and shows the following features.

<Physical and Chemical Properties of Icariin>

Morphology: pale yellow micro-crystal

Positive FAB-MS: 677[M+H]

$^1$H NMR: (DMSO-d6) δ: 0.81 (3H, d, J=6 Hz, Rham-6), 1.61 & 1.69 (6H, br s, Me-11), ca 3.1-3.3 (m), 3.33 (1H, br d-like, ca 5), ca 3.4-3.6 (m), ca 3.7-3.76 (1H, m), 3.86 (3H, s, OMe-4'), 4.01 (1H, br, H2''), 5.00 (1H, d, 7.5, H1'''), 5.19 (1H, br t, 7, H10), 5.30 (1H, d, J=1.5 Hz, H1''), 6.64 (1H, s, H6), 7.12 (2H, d, 9, H3',5'), 7.89 (2H, d, 9, H2',6'), 12.53 (1H, s, OH-5).

$^{13}$C-NMR: (DMSO-d6) δ: 153.0, 135.7, 178.3, 160.5, 98.2, 161.4, 108.4, 157.3, 105.6, 122.2, 130.5, 114.1, 160.5, 114.1, 130.5, 21.1, 122.3, 131.1, 25.4, 17.5, 102.0, 70.4, 70.6, 69.7, 70.1, 17.9, 100.6, 73.4, 76.7, 71.2, 76.7, 60.7, 55.5.

Acid hydrolysates: icaritin, glucose, rhamnose

Example 2

Preparation and Identification of Icaritin, Icarisides I and II

<Preparation of Icaritin, Icariside I and II by Acid Hydrolysis>

20 g of the extract prepared in Example 1 was taken in 1N HCl-50% methanol solution (v/v) in an amount of 20 times (v/w) of its amount and heated to reflux in a water bath at 80° C. for 8 hours to hydrolyze sugars bonded to icariin. The reaction was concentrated under pressure to remove the solvent. The residue was added to ethanol (200 ml), stirred (3 times) and subjected to filtration to remove precipitated salts. The filtrate was concentrated under pressure to obtain a crude product, which was then separated by silica gel column chromatography (chloroform:methanol=8:1 to 4:1) to give 0.9 g of icaritin, 0.7 g of icariside 1 and 0.5 g of icariside II.

<Preparation of Icaritin, Icarisides I and II by Base Hydrolysis>

20 g of the extract prepared in Example 1 was taken in dry pyridine (500 ml) and sodium methoxide (powder, 10 g) was added thereto. The solution was heated to reflux in a water bath at 80° C. for 8 hours to hydrolyze sugars bonded to icariin. The reaction was concentrated under pressure to remove the solvent. The residue was added to ethanol (200 ml), stirred (3 times) and subjected to filtration to remove precipitated salts. The filtrate was concentrated under pressure to obtain a crude product, which was then separated by silica gel column chromatography (chloroform:methanol=8:1 to 4:1) to give 0.6 g of icaritin, 0.7 g of icariside 1 and 0.8 g of icariside II.

<Preparation of Icaritin, Icariside I and II by Enzyme Hydrolysis>

20 g of the extract prepared in Example 1 was taken in 100 ml of 0.1M acetic acid buffer solution (pH 4.5) and 2.5 g of enzymes (0.5 g of hesperidinase, 0.5 g of naringinase, 0.5 g of cellulase, 0.2 g of β-glucuronidase, 0.5 g of β-galactosidase, 0.3 g of amyloglucosidase; supplied by Sigma) was added thereto. The solution was stirred in a water bath at 37° C. for 48 hours. When icariin completely disappeared by periodically confirming by thin layer chromatography, the reaction was finished by heating in hot water (80 to 100° C.) for 10 minutes. The reaction was concentrated under pressure to remove the solvent. The residue was added to ethanol (200 ml), stirred (3 times) and subjected to filtration to remove precipitated salts. The filtrate was concentrated under pressure to obtain a crude product, which was then separated by silica gel column chromatography (chloroform:methanol=8:1 to 4:1) to give 1.1 g of icaritin, 1.2 g of icariside 1 and 0.9 g of icariside II.

<Preparation of Icaritin, Icariside I and II Using Microorganism>

20 g of the extract prepared in Example 1 was taken in ionized water, sterilized at about 121° C. for 30 minutes, cooled to about 30° C., inoculated with *Aspergillus niger* KCCM 11885, which had been cultured, in an amount of 5 to 10% based of the total amount of the solution and cultivated at 30° C. for 5 days, preferably 5 days. When icariin completely disappeared by confirming the elimination rate of icariin by thin layer chromatography, the reaction was ended. The resulting culture fluid was centrifuged at 5,000 to 10,000 rpm. The precipitation was washed 3 times with distilled water and centrifuged to obtain precipitation. The precipitation was added to ethanol (200 ml), stirred (3 times) and subjected to filtration to remove residue. The filtrate was concentrated under pressure to obtain a crude product, which was then separated by silica gel column chromatography (chloroform:methanol=8:1 to 4:1) to give 0.8 g of icaritin, 0.7 g of icariside 1 and 0.8 g of icariside II.

<Identification of Icariside I>

20 g of the extraction prepared by enzyme hydrolysis was purified by silica gel column chromatography, charged with silica gel 100 g. Here, chloroform and methanol were used as the eluting solvents. Fractions were obtained by increasing the ratio of chloroform and methanol from 10:1 to 2:1 and 1.8 g of icariside I was produced therefrom. The resulting product was identified (Varian Gemini 2000 300 MHz, Varian) and shows the following features.

<Physical and Chemical Properties of Icariside I>

Morphology: pale yellow micro-crystal

Positive FAB-MS: 531 [M+H]

$^1$H NMR: (DMSO-d6) δ: 1.70, 1.83 (ea. 3H, s, Me-4",5"), 2.90 (2H, H1"), 3.87 (3H, s, OMe), 3.83-5.40 (m, sugar protons), 6.64 (1H, s, H6), 7.16 (2H, d, 9, H3',5'), 8.23 (2H, d, 9, H2',6').

$^{13}$C-NMR: (DMSO-d6) δ: 146.9, 136.2, 176.5, 160.1, 97.5, 160.6, 108.1 152.7, 104.5, 123.4, 129.3, 114.1, 158.5, 114.1, 129.3, 21.5, 122.3, 131.1, 25.4, 17.9, 100.5, 73.4, 76.7, 69.7, 77.2, 60.7, 55.4.

Acid hydrolysates: icaritin, glucose

<Identification of Icariside II>

20 g of the extraction prepared by enzyme hydrolysis was purified by silica gel column chromatography, charged with silica gel 100 g. Here, chloroform and methanol were used as the eluting solvents. Fractions were obtained by increasing the ratio of chloroform and methanol from 10:1 to 2:1 and 1.5 g of icariside II was produced therefrom. The resulting product was identified (Varian Gemini 2000 300 MHz, Varian) and shows the following features.

<Physical and Chemical Properties of Icariside II>

Morphology: pale yellow micro-crystal

Positive FAB-MS: 515[M+H]

$^1$H NMR: (DMSO-d6) δ: 0.79 (3H, d, 6, Me-5"), 1.63 & 1.68 (6H, br s, Me-11), 3.03 (1H, qd, 6, 9.5, H5"), 3.14 (1H, dd, 9, 9.5, H4"), ca 3.4 (2H-9, overlapping with the signals of H2O), 3.47 (1H, br, H3"), 3.85 (3H, s, OMe-4'), 3.98 (1H, br, H2"), 5.15 (1H, br t, 7, H10), 5.26 (1H, d, 1.5, H1"), 6.31 (1H, s, H6), 7.12 (2H, d, 9, H3',5'), 7.86 (2H, d, 9, H2',6'), 12.52 (1H, s, OH-5).

$^{13}$C-NMR: (DMSO-d6) δ: 156.2, 133.8, 177.1, 103.6, 158.1, 97.8, 160.9, 105.4, 153.8, 21.0, 121.7, 130.3, 17.6, 25.2, 121.8, 129.7, 113.5, 160.5, 55.2, 101.4, 69.7, 70.0, 70.2, 70.8, 17.3.

Acid hydrolysates: icaritin, rhamnose

<Identification of Icaritin>

20 g of the extraction prepared by enzyme hydrolysis was purified by silica gel column chromatography, charged with silica gel 100 g. Here, chloroform and methanol were used as the eluting solvents. Fractions were obtained by increasing the ratio of chloroform and methanol from 10:1 to 2:1 and 2.4 g of icaritin was produced therefrom. The resulting product was identified (Varian Gemini 2000 300 MHz, Varian) and shows the following features.

<Physical and Chemical Properties of Icaritin>

Morphology: Pale yellow micro-crystal

Positive FAB-MS: 369[M+H]

$^1$H NMR: (DMSO-d6, 300 MHz) δ: 3.82 (3H, s, OMe), 1.62 (3H, s, Me-5"), 1.75 (3H, s, Me-4"), 5.14 (1H, t, 6, H2"), 3.24 (2H, d, 6, H1"), 7.08 (2H, d, 8.7, H3',5'), 8.10 (2H, d, 8.7, H2',6'), 6.27 (1H, s, H6).

Experimental Example 1

Test of Anti-Oxidant Effect of Icariin, Icaritin, Icariside I and Icariside II (DPPH Test)

A method for evaluating anti-oxidant effect through change of absorption generated by reduction of the organic radical DPPH (1,1-diphenyl-2-picryl hydrazyl) (while antioxidant is oxidized) is used. The change of absorption, which was decreased when the oxidization of DPPH was inhibited, was measured, as compared to the control. The concentration, upon which the absorption was 50% or less than the absorption of the control, was defined as an effective anti-oxidant concentration.

190 μl of 100 μM (in ethanol) DPPH solution and 10 μl of icariin, icariside I, icariside II and icaritin, identified in Examples 1 to 2, and control sample were mixed to form reactants, which were then reacted at 37° C. for 30 minutes. The absorption was measured at 540 nm. The control sample was synthesized anti-oxidant Trolox, commonly used.

The result of DPPH analysis of each substance is shown in Table.

TABLE 1

DPPH analysis (inhibition %)
(IC50: concentration, upon which the absorption
is decreased to 50% by addition of each substance)

| Sample | IC50 (μM) |
| --- | --- |
| Icariin | 49.59 |
| Icariside I | 7.78 |
| Icariside II | 7.15 |
| Icaritin | 6.75 |
| Trolox | 8.63 |

As shown in Table 1, icaritin, icarisides I and II according to the present invention showed better activity than icariin and even better anti-oxidant effect than Trolox.

Experimental Example 2

Test of Inhibition Effect of Icariin, Icaritin, Icariside I and Icariside II on Reactive Oxygen Species (ROS) Using Fluorescent Material The cell lines used in the test was Human keratinocytes HaCaT cell line. The cells were distributed to a 96 well black plate for fluorescence measurement at $2.0 \times 10^4$ per each well and cultured in DMEM (Dulbeccos Modification of Eagles Medium, FBS 10%) supplemented with penicillin/streptomycin at 37° C., 5% $CO_2$ for 1 day, followed by treatment with test samples. Serum free DMEM (FBS free) supplemented with penicillin/streptomycin as shown in Table 2 was used for cultivation of the medium which had been treated with samples. The cultivation was performed at 37° C., 5% $CO_2$ for 1 day.

After cultivation of 24 hours with test samples, the plate was washed with HCSS (HEPES-buffered control salt solution) to remove the medium and the HCSS was treated with 100 μl of 20 μM DCFH-DA (2',7'-dichlorodihydro-fluorescein diacetate, Molecular Probes, Inc). Then, the plate was kept under conditions of 37° C., 5% $CO_2$ for 20 minutes and washed with HCSS. Next, the plate was treated with 100 μl of HCSS comprising samples at different concentrations and the fluorescence intensity of DCF (dichlorofluorescein), which had been oxidized to ROS at the early stage, was measured using a fluorescent plate reader (Ex=485 nm, Em=530 nm). The fluorescence, right after the irradiation of UVB (30 mJ/cm$^2$) or 3 hours later of the irradiation, was measured using a fluorescent plate reader (Ex=485 nm, Em=530 nm).

As control, Trolox was used.

The result of inhibition effect of each sample on ROS production is shown in Table 2.

TABLE 2

Inhibition effect on ROS production (control %)

| Concentration (uM) | icariin | icariside I | icariside II | icaritin | Trolox |
| --- | --- | --- | --- | --- | --- |
| 50 | 86.3 | 43.8 | 46.6 | 43.2 | 58.5 |
| 25 | 88.6 | 54.8 | 56.6 | 51.7 | 73.3 |
| 12.5 | 89.7 | 61.4 | 62.0 | 61.5 | 74.6 |
| 6.25 | 98.1 | 65.6 | 63.2 | 68.2 | 76.9 |

As shown in Table 2, icaritin, icarisides I and II according to the present invention showed better activity than icariin and even better inhibition effect on ROS production than Trolox.

Experimental Example 3

Promotion Effect of Icariin, Icaritin, Icariside I and Icariside II on Collagen Biosynthesis The promotion effect of icariin, icaritin, icariside I and icariside II, identified in Examples 1 to 2, on collagen biosynthesis was compared to tocopherol and EGCG.

Firstly, fibroblasts (PromoCell, Germany) were seeded in a 24 well plate at a level of $10^5$ per well and cultured until they grew up to 90%. The cells were cultured in serum free DMEM for 24 hours, treated with icariin, icariside I, icariside II and icaritin, identified in Examples 1 to 2, tocopherol and EGCG dissolved in serum free medium at a molar concentration of 10- and cultivated in a $CO_2$ medium for 24 hours. The supernatant was taken and examined for increase and decrease of procollagen using procollagen type (I) ELISA kit (proc/; ollagen type (I)). The result is shown in Table 3, in which the synthesis is compared to 100 of the non-treatment group.

TABLE 3

| Treatment group | Synthesis (%) |
| --- | --- |
| Non-treatment group | 100 |
| Tocopherol | 118 |
| EGCG | 125 |
| Icariin | 117 |
| Icariside I | 145 |
| Icariside II | 138 |
| Icaritin | 146 |

As shown in Table 3, icaritin, icarisides I and II according to the present invention showed greater increase of collagen biosynthesis than icariin and even better effect than the positive control.

Experimental Example 4

Inhibition Effect of Icariin, Icaritin, Icariside I and Icariside II on Expression of Collagenase The inhibition effect of icariin, icaritin, icariside I and icariside II, identified in Examples 1 to 2, on collagen expression (production) was compared to tocopherol and EGCG, as follows.

Firstly, human fibroblasts were seeded in a 96-well microtiter plate containing DMEM supplemented with 2.5% fetal bovine serum at a level of 5000 cells per well and cultured until they grew up to 90%. The cells were cultured in serum free DMEM for 24 hours, treated with icariin, icariside I, icariside II and icaritin, identified in Examples 1 to 2; tocopherol and EGCG, as test materials, dissolved in serum free DMEM medium at a molar concentration of $10^{-4}$ and cultivated for 24 hours to take culture fluid.

Then, the culture fluid was examined for formation of collagenase using a commercially available collagenase measuring kit (Amorsham pharmacia, USA).

Firstly, the taken cell culture fluid was added to the 96-well plate having the primary collagenase antibody evenly applied and left for antigen-antibody reaction in a thermostat for 3 hours. After 3 hours, the secondary collagen antibody having a chromophore bonded thereto was added to the 96-well plate and left for reaction for 15 minutes. After 15 minutes, a color developing agent was added and left for 15 minutes. Then, 1M sulphuric acid was added to quit the reaction (color development), upon which the color of the reaction became yellow. The yellow level varied according to the progress of the reaction.

The absorption of the 96-well plate of the yellow color was measured at 405 nm using a spectrophotometer. The expression of collagenase was calculated according to the following Equation I. Here, the absorption of the control was the absorption of the cell culture fluid taken from the group which had not been treated with the test materials.

Expression of collagenase (%) $(A/B) \times 100$      [Equation I]

(A: absorption of cells treated with the test materials B: absorption of control)

Meanwhile, the result of measurement of inhibition effect of the test materials on collagenase expression in human fibroblasts is shown in Table 4, in which in which the expression of collagenase is compared to 100 of the non-treatment group.

TABLE 4

| Test materials | Expression of collagenase (%) |
|---|---|
| non-treatment group | 100 |
| tocopherol (positive control) | 75 |
| EGCG (positive control) | 60 |
| Icariin | 81 |
| icariside I | 64 |
| icariside II | 66 |
| Icaritin | 66 |

As shown in Table 4, it was confirmed that icaritin, icarisides I and II according to the present invention effectively inhibited the collagenase expression.

Experimental Example 5

Inhibition Effect of Icariin, Icaritin, Icariside I and Icariside II on Expression of Elastase The inhibition effect of icariin, icaritin, icariside I and icariside II, identified in Examples 1 to 2, on elastase expression (production) was compared to tocopherol and EGCG, as follows.

Firstly, human fibroblasts were seeded in a 96-well microtiter plate containing DMEM supplemented with 2.5% fetal bovine serum at a level of 5000 cells per well and cultured until they grew up to 90%. The cells were cultured in serum free medium for 24 hours, treated with icariin, icariside I, icariside II and icaritin, identified in Examples 1 to 2, tocopherol and EGCG, as test materials, dissolved in serum free DMEM medium at a molar concentration of $10^{-4}$ and cultivated for 24 hours to take culture fluid.

Then, the culture fluid was examined for formation of elastase using a commercially available elastase measuring kit (Amorsham pharmacia, USA).

Firstly, the taken cell culture fluid was added to the 96-well plate having the primary elastase antibody evenly applied and left for antigen-antibody reaction in a thermostat for 3 hours. After 3 hours, the secondary collagen antibody having a chromophore bonded thereto was added to the 96-well plate and left for reaction for 15 minutes. After 15 minutes, a color developing agent was added and left for 15 minutes. Then, 1M sulphuric acid was added to quit the reaction (color development), upon which the color of the reaction became yellow. The yellow level varied according to the progress of the reaction.

The absorption of the 96-well plate of the yellow color was measured at 405 nm using a spectrophotometer. The expression of elastase was calculated according to the following Equation II. Here, the absorption of the control was the absorption of the cell culture fluid taken from the group which had not been treated with the test materials.

Expression of elastase (%)=$(A/B) \times 100$      [Equation II]

(A: absorption of cells treated with the test materials B: absorption of control)

Meanwhile, the result of measurement of inhibition effect of the test materials on elastase expression in human fibroblasts is shown in Table 5, in which the expression of elastase is compared to 100 of the non-treatment group.

TABLE 5

| Test materials | Expression of elastase (%) |
|---|---|
| Non-treatment group | 100 |
| Tocopherol (positive control) | 88 |
| EGCG (positive control) | 68 |
| Icariin | 87 |
| Icariside I | 56 |
| Icariside II | 63 |
| Icaritin | 55 |

As shown in Table 5, it was confirmed that icaritin, icarisides I and II according to the present invention effectively inhibited the elastase expression Experimental Example 6

Measurement of Inhibition Effect of Icariin, Icaritin Icariside I and Icariside II on Melanin Synthesis Using Pigment Cell of Mouse In order to examine the inhibition effect of icariin, icaritin, icariside I and icariside II, identified in Examples 1 to 2, on melanin synthesis, pigment cells of mouse were used.

Firstly, pigment cells (Mel-Ab cell) of rat derived from C57BL/6 mouse (Dooley, T. P. et al, Skin pharmacol, 7, pp 188-200) were cultured in DMEM supplemented with 10% fetal bovine serum, 100 nM 2-O-tetradecanoylphorbyl)-13-acetate and 1 nM cholera toxin at 37° C., 5% $CO_2$. The cultured Mel-Ab cells were separated with 0.25% trypsin-EDTA and cultured in a 24-well plate at a concentration $10^5$ (cells/well). After 2 days, 10 ppm of respective test materials of hydroquinone, icariin, icariside I, icariside II and icaritin, identified in Examples 1 and 2 were added for continuous 3 days and cultivated. Here, hydroquinone was a positive control. Then, the culture fluid was removed and washed with PBS. The cells were lysed with 1N sodium hydroxide and absorption was measured 400 nm. The inhibition rate of melanin synthesis was calculated according to the following Equation III and the result is shown in Table 6 (Dooley's method).

Inhibition of melanin synthesis (%)=100−{(Absorption of each test group/Absorption of control group)×100}      [Equation III]

TABLE 6

| Test materials | Inhibition of melanin synthesis (%) |
| --- | --- |
| Non-treatment group | 100.0 |
| Icariin | 84.5 |
| Icariside I | 38.6 |
| Icariside II | 38.2 |
| Icaritin | 39.5 |
| Hydroquinone (positive control) | 41.1 |

As shown in Table 6, it was confirmed that icaritin, icarisides I and II prepared in Examples 1 and 2 according to the present invention showed more excellent inhibition effect on melanin synthesis than icariin identified in Example 1. Particularly, icaritin, icarisides I and II showed a similar inhibition effect on melanin synthesis to hydroquinone.

Experimental Example 7

Test of Whitening Effect of Icariin, Icaritin, Icariside I and Icariside II on Human Skin The following experiment was performed to exam the whitening effect of icariin, icariside I, icariside II and icaritin, identified in Examples 1 to 2, on human skin.

Firstly, 12 healthy males were enlisted for the test. They had opaque tape with a 1.5 cm hole attached on the upper arm. UV rays 1.5 to 2 times greater than the minimal erythema dose were irradiated to induce darkening of the skin.

After irradiation of UV rays, 1% of icariin, icariside I, icariside II and icaritin (solvent: 1,3-butyleneglycol:ethanol=7:3), 1% of hydroquinone, 1% of solvent (vehicle) (negative control) 1% were applied on the skin and other part had nothing applied thereon. For 10 weeks, the change was observed. Every 1 week, the color of the skin was measured by colorimeter CR2002 (Japan, Minolta)

Then, the difference of skin color ($\Delta L^*$) between the point when the application of the test material was initiated and the point when the application of the test material was completed was calculated according to the following equation and the result is shown in Table 7. Meanwhile, the whitening effect was determined by comparison of $\Delta L^*$ between the sample applied part and the control. When $\Delta L^*$ value is about 2, the whitening of the pigmentation was significant. When $\Delta L^*$ is over 1.5, it was considered that the sample had whitening effect.

$$\Delta L^* = (L^* \text{at the point when the application is completed}) - (L^* \text{at the point when the application is initiated}) \quad [\text{Equation 4}]$$

TABLE 7

| Test sample | Whitening effect ($\Delta L^*$) |
| --- | --- |
| Icariin | 1.10 ± 0.13 |
| icariside I | 1.88 ± 0.17 |
| icariside II | 1.83 ± 0.25 |
| Icaritin | 1.89 ± 0.25 |
| Hydroquinone (positive control) | 1.90 ± 0.11 |
| Solvent (Vehicle, negative control) | 0.50 ± 0.15 |

As shown in Table 7, the icariin, icariside I, icariside II and icaritin prepared in Examples 1 to 2 according to the present invention showed brightness of skin similar to hydroquinone. It is because the above materials improved the pigmentation caused by UV rays and brightened the skin color.

Now, the formulation of the composition according to the present invention is explained by the following formulation examples. However, it should be understood that the examples are only for illustration of the present invention and the present invention is not limited thereto.

Formulation Example 1

Preparation of Soap

TABLE 8

| Ingredient | Content (wt %) |
| --- | --- |
| Icariside I | 1.00 |
| Oil | suitable amount |
| Sodium hydroxide | suitable amount |
| Sodium chloride | suitable amount |
| Perfume | small amount |

The ingredients in the described mixing ratio were compounded with purified water to make the total weight of 100.

Formulation Example 2

Preparation of Lotion

TABLE 9

| Ingredient | Content (wt %) |
| --- | --- |
| Icariside II | 3.00 |
| L-ascorbic acid-2-phosphate magnesium | 1.00 |
| Water soluble collagen (1% water solution) | 1.00 |
| Sodium citrate | 0.10 |
| Citric acid | 0.05 |
| Licorice extract | 0.20 |
| 1,3-butylene glycol | 3.00 |

The ingredients were mixed in the above-described mixing ratio and purified water was added to make 100 of the total weight.

Formulation Example 3

Preparation of Cream

TABLE 10

| Ingredient | Content (wt %) |
| --- | --- |
| Icaritin | 1.00 |
| Polyethylene glycol monostearate | 2.00 |
| Self-emulsible stearic acid Glycerine monostearate | 5.00 |
| Cetyl alcohol | 4.00 |
| Squalene | 6.00 |
| Glycerol | 6.00 |
| sphingoglycolipid | 1.00 |
| 1,3-butylene glycol | 7.00 |

The ingredients were mixed in the above-described mixing ratio and purified water was added to make 100 of the total weight.

Formulation Example 4

Preparation of Pack

TABLE 11

| Ingredient | Content (wt %) |
| --- | --- |
| Icariside I | 5.00 |
| Polyvinyl alcohol | 13.00 |
| L-ascorbic acid-2-phosphate magnesium | 1.00 |
| lauroyl hydroxyproline | 1.00 |
| Water soluble collagen (1% water solution) | 2.00 |
| 1,3-butylene glycol | 3.00 |
| Ethanol | 5.00 |

The ingredients were mixed in the above-described mixing ratio and purified water was added to make 100 of the total weight.

Formulation Example 5

Preparation of Cosmetic Liquid

TABLE 12

| Ingredient | Content (wt %) |
| --- | --- |
| icariside II | 2.00 |
| hydroxyethylene cellulose (2% water solution) | 12.00 |
| xanthan gum (2% water solution) | 2.00 |
| 1,3-butylene glycol | 6.00 |
| Conc. Glycerin | 4.00 |
| Sodium hyaluonate (1% water solution) | 5.00 |

The ingredients were mixed in the above-described mixing ratio and purified water was added to make 100 of the total weight.

Formulation Example 6

Preparation of Dispersion

TABLE 13

| Ingredient | Content (unit: mg) |
| --- | --- |
| icaritin | 300 |
| lactose | 100 |
| Talc | 10 |

The above-described ingredients were mixed and filled into an air-tight bag.

Formulation Example 7

Preparation of Tablet

TABLE 14

| Ingredient | Content (unit: mg) |
| --- | --- |
| Icariside I | 50 |
| Corn starch | 100 |
| Lactose | 100 |
| Magnesium stearate | 2 |

The above-described ingredients were mixed according to a commonly used method for preparing tablets.

Formulation Example 8

Preparation of Capsule

TABLE 15

| Ingredient | Content (unit: mg) |
| --- | --- |
| Icariside II | 50 |
| Corn starch | 100 |
| Lactose | 100 |
| Magnesium stearate | 2 |

The ingredients were compounded according to a commonly used method for preparing capsules and filled into gelatin capsules.

Formulation Example 9

Preparation of Injection Solution

TABLE 16

| Ingredient | Content (unit: mg) |
| --- | --- |
| Icaritin | 50 |
| Sterilized distilled water for injection | Suitable amount |
| pH controller | Suitable amount |

The ingredients were compounded according to a commonly used method for preparing an injection solution to produce one ample (2 ml).

Formulation Example 10

Preparation of Solution

TABLE 17

| Ingredient | Content |
| --- | --- |
| icariside I | 100 mg |
| Isomerized Sugar | 10 g |
| Mannitol | 5 g |
| Purified water | Suitable amount |

The ingredients were dissolved in purified water according to a commonly used method for preparing a solution. After lemon incense was added, the ingredients were mixed and purified water added to the mixture to make the total volume of 100 ml. The resulting solution was then filled into an amber bottle.

INDUSTRIAL APPLICABILITY

As described above, it has been confirmed that the cosmetic composition containing hydrolysates of icariin, which is prepared by hydrolyzing icariin, a flavonoid ingredient in an extract from a plant of the *Epimedium* genus, with an acid, a base, an enzyme or a microorganism producing the enzyme, has anti-oxidant effect to inhibit production of DPPH and ROS, anti-aging effect by promotion of collagen biosynthesis, inhibition of expression of elastase and collagenase, and whitening effect by inhibition of melanin production and improvement of pigmentation caused by ultraviolet rays (UV). Therefore, the hydrolysates of icariin according to the present invention may be usefully used as a cosmetic composition or a pharmaceutical composition for anti-oxidant, anti-aging, whitening and anti-wrinkle effects.

The invention claimed is:

1. A method of inhibiting melanin production comprising applying to the skin of a subject an effective amount of a composition comprising an acid hydrolysate, base hydrolysate, enzyme hydrolysate or microorganism hydrolysate of Icariin and has the structure of a compound of the formula I:

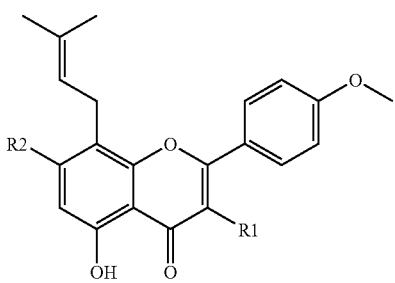

[Formula 1]

in which R1 is OH or —O-rhamnopyranose, R2 is OH or —O-glucopyranose, provided that the sugar moieties are attached through the oxygen of the sugar ring and further provided both R1 and R2 are not —O-rhamnopyranose or —O-glucopyranose at the same time.

2. A method of reducing skin pigmentation and whitening the skin comprising applying to the skin of a subject an effective amount of a cosmetic composition comprising an acid hydrolysate, base hydrolysate, enzyme hydrolysate or microorganism hydrolysate of Icariin and has the structure of a compound of the formula I:

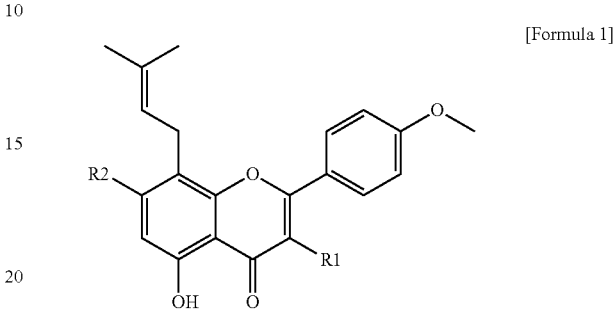

[Formula 1]

in which R1 is OH or —O-rhamnopyranose, R2 is OH or —O-glucopyranose, provided that the sugar moieties are attached through the oxygen of the sugar ring and further provided both R1 and R2 are not —O-rhamnopyranose or —O-glucopyranose at the same time.

* * * * *